US00PP17016P3

(12) United States Plant Patent

Gerdts et al.

(10) Patent No.: US PP17,016 P3

(45) Date of Patent: Aug. 22, 2006

(54) PEACH TREE 'BURPEACHTWENTYONE'

(50) Latin Name: *Prunus persica*
Varietal Denomination: Burpeachtwentyone

(75) Inventors: Timothy J. Gerdts, Kingsburg, CA (US); John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 94 days.

(21) Appl. No.: 11/011,392

(22) Filed: Dec. 14, 2004

(65) Prior Publication Data

US 2006/0130198 P1 Jun. 15, 2006

(51) Int. Cl.
*A01H 5/00* (2006.01)

(52) U.S. Cl. ..... Plt./197

(58) Field of Classification Search ..... Plt./197
See application file for complete search history.

(56) References Cited

U.S. PATENT DOCUMENTS

PP4,399 P * 3/1979 Merrill et al. ..... Plt./198
PP7,290 P * 8/1990 Zaiger et al. ..... Plt./197

* cited by examiner

*Primary Examiner*—Kent Bell
*Assistant Examiner*—W C Haas
(74) *Attorney, Agent, or Firm*—Wells St. John, P.S.

(57) ABSTRACT

A new and distinct variety of peach tree *Prunus persica,* which is denominated varietally as 'Burpeachtwentyone', and which produces an attractively colored yellow-fleshed, clingstone peach which is mature for harvesting approximately July 5 to July 15 under the ecological conditions prevailing in the San Joaquin Valley of central California.

1 Drawing Sheet

Botanical designation: *Prunus persica.*
Variety denomination: Burpeachtwentyone.

BACKGROUND OF THE NEW VARIETY

The present invention relates to a new, novel and distinct variety of peach tree, *Prunus persica,* and which has been denominated varietally as 'Burpeachtwentyone'.

ORIGIN

The present variety of peach tree resulted from an on-going program of fruit and nut tree breeding. The purpose of this program is to improve the commercial quality of deciduous fruit and nut varieties, and rootstocks, by creating and releasing promising selections of *Prunus, Malus,* and *Regia* species. To this end we make both controlled and hybrid cross pollinations each year in order to produce seedling populations from which improved progenies are evaluated and selected.

The seedling, 'Burpeachtwentyone' was originated by us and selected from a population of seedlings growing in our experimental orchards located near Fowler, Calif. The seedlings, grown on their own roots, were derived from open-pollinated seeds of our variety 'A25.045'. A25.045 (unpatented) was derived from a cross of the yellow-fleshed freestone peach tree 'Fairtime' (unpatented, USDA), which was used as the seed parent; and the 'Rich Lady' peach tree, (U.S. Plant Pat. No. 7,290), which was used as the pollen parent. Thereafter seeds from 'A25.045' were planted in September of 1997. One seedling which is the present variety, exhibited especially desirable characteristics, and was designated as 'E25.069'. This seedling was marked for subsequent observation. After the 1999 fruiting season, the new variety of peach tree was selected for advanced evaluation and repropagation.

ASEXUAL REPRODUCTION

Asexual reproduction of this new and distinct variety of peach tree was accomplished by budding the new peach tree to 'Nemaguard' Rootstock (unpatented). This was performed by us in our experimental orchard which is located near Fowler, Calif. Subsequent evaluations have shown those asexual reproductions run true to the original tree. All characteristics of the original tree, and its fruit, were established, and appear to be transmitted through succeeding asexual propagations.

SUMMARY OF THE VARIETY

'Burpeachtwentyone' is a new and distinct variety of peach tree, which is considered of large size, and which has vigorous growth. This new peach tree is also a regular and productive bearer of relatively large, firm, yellow-fleshed, clingstone fruit which have good flavor and eating qualities. This new tree has a medium chilling requirement of approximately 650 hours, and further produces relatively uniformly sized fruit throughout the tree. In addition to the foregoing, the fruit of the new tree also appears to have good handling and shipping qualities. The 'Burpeachtwentyone' peach tree bears fruit which are ripe for commercial harvesting and shipment on approximately July 5 to July 15 under the ecological conditions prevailing in the San Joaquin Valley of central California. In relative comparison with the clingstone peach tree 'A25.045', which is the seed parent, the present new variety of peach tree bears fruit which ripen about 10 or more days earlier at the same geographical location. In relative comparison to the freestone peach, 'Elegant Lady' (U.S. Plant Pat. No. 4,399), which is the most similar variety known to the inventors at this time, the present new variety produces clingstone fruit and exhibits very few split pits, whereas the pit of the 'Elegant Lady' peach is a freestone and split pits are quite common.

BRIEF DESCRIPTION OF THE DRAWING

The accompanying drawing, which is provided, is a color photograph of the new peach tree variety. The photograph depicts two whole mature fruit, and one mature fruit dissected substantially in the equatorial plane, and which reveals the flesh and the stone characteristics thereof. The external coloration of the fruit as shown is sufficiently matured for harvesting and shipment. Additionally, the photograph displays a sample vegetative shoot bearing typical leaves, and a typical stone, with the flesh removed. The colors in this photograph are as nearly true as is reasonably possible in a color representation of this type. Due to chemical development, processing and printing, the leaves and fruit depicted in these photographs may or may not be accurate when compared to the actual specimen. For this reason, future color references should be made to the color plates (Royal Horticultural Society) and descriptions provided hereinafter.

DETAILED DESCRIPTION

Referring more specifically to the pomological details of this new and distinct variety of peach tree, the following has been observed during the sixth fruiting season under the ecological conditions prevailing at orchards which are located near the town of Fowler, county of Fresno, state of California. All major color code designations are by reference to The R.H.S. Colour Chart (Fourth Edition) provided by The Royal Horticultural Society of Great Britain. Common color names are also occasionally used.

Tree:

*Size.*—Generally — Considered medium-large as compared to other common commercial peach cultivars ripening in the late season of maturity. The tree of the present variety was pruned to a height of approximately 305.0 cm to about 310.0 cm at maturity.

*Vigor.*—Considered moderately vigorous. The present peach tree variety grew from about 125.0 cm to about 135.0 cm in height during the first growing season. The new variety was pruned to a height of approximately 120.0 cm during the first dormant season, and primary scaffolds were then selected for the desired tree structure.

*Productivity.*—Productive. Fruit set varies from about 1.5 to several times more than the desired crop load. The fruit set is spaced by thinning to develop the remaining fruit into the desired market sized fruit. The number of the fruit set varies with the prevailing climatic conditions, and cultural practices employed during the bloom period, and is therefore not distinctive of the variety.

*Bearer.*—Regular. Fruit set has been heavy during the years of observation, and thinning was necessary during the past 6 years.

*Form.*—Upright, and pruned into a vase shape.

*Density.*—Considered medium dense. It has been discovered that pruning the branches from the center of the tree to obtain a resulting vase shape allows for air movement and appropriate amounts of sunlight to enhance fruit color and renewal of fruiting wood throughout the tree.

*Hardiness.*—The present tree was grown and evaluated in USDA Hardiness Zone 9. Winter chilling requirements of the new tree are approximately 700 hours below 7.0 degrees C. The variety appears to be hardy under typical central San Joaquin Valley climatic conditions.

Trunk:

*Diameter.*—Approximately 14.6 cm in diameter when measured at a distance of approximately 15.24 cm above the soil level. This measurement was taken at the end of the seventh growing season.

*Bark texture.*—Considered moderately rough, with numerous folds of papery scarfskin being present.

*Lenticels.*—Numerous flat, oval lenticels are present. The lenticels range in size from approximately 4.0 to about 5.0 millimeters in width, and from about 1.0 to about 2.0 millimeters in height.

*Lenticel color.*—Orange brown, (RHS Greyed-Orange Group N172 D).

*Bark coloration.*—Variable, but it is generally medium grey-brown, (RHS Greyed-Orange Group 175 A).

Branches:

*Size.*—Considered medium for the variety.

*Diameter.*—Average as compared to other peach varieties. The branches have a diameter of about 9.7 centimeters when measured during the fifth year after grafting.

*Surface texture.*—Average, and appearing furrowed on wood which is several years old.

*Crotch angles.*—Primary branches are considered variable and are between about 46 to about 52 degrees when measured from the horizontal axis. This particular characteristic is not considered distinctive of the variety, however.

*Current season shoots.*—Surface texture — Substantially glabrous.

*Internode length.*—Approximately 2.2 to about 2.4 cm.

*Color of mature branches.*—Medium brown, (RHS Greyed-Orange N167 B).

*Current seasons shoots.*—Color — Light green, (RHS Yellow-Green Group 146 C). The color of new shoot tips is considered a bright and shiny green (RHS Green Group 141 C).

Leaves:

*Size.*—Considered medium large for the species. Leaf measurements have been taken from vigorous, upright, current-season growth at approximately mid-shoot.

*Leaf length.*—Approximately 160.0 to about 168.0 millimeters.

*Leaf width.*—Approximately 35.0 to about 40.0 millimeters.

*Leaf base shape.*—Reasonably uniform in margin symmetry relative to the leaf longitudinal axis.

*Leaf form.*—Lancelolate.

*Leaf tip form.*—Acuminate.

*Leaf color.*—Upper Leaf Surface — Dark green, (approximately RHS Green Group 139 A).

*Leaf texture.*—Glabrous.

*Leaf color.*—Lower Surface — Medium green, (RHS Yellow-Green Group 146 A).

*Leaf venation.*—Pinnately veined.

*Mid-vein.*—Color — Light yellow green, (RHS Yellow-Green Group 150 C).

*Leaf margins.*—Slightly undulating.

*Form.*—Considered finely crenate.

*Uniformity.*—Considered generally uniform.

*Leaf petioles.*—Size — Considered medium long. Length — About 6.0 to about 11.0 mm. Diameter — About 1.5 to about 2.0 mm. Color — Pale green, (RHS Yellow-Green Group N144 B).

*Leaf glands.*—Size — Considered small. Approximately 1.0 mm in length, and about 1.0 mm in height. Number — Generally one gland per margin side. Occasionally two glands per margin side. Type — Reniform. Color — Considered a dark tan (RHS Grey-Brown Group 199 C).

*Leaf stipules.*—Size — Medium large for the variety. Number — Typically 2 per leaf bud and up to 6 per shoot tip. Form — Lanceolate in form and having a serrated margin. Color — Green, (RHS Yellow-Green Group 146 D) when young, but graduating to a brown color, (RHS Greyed-Orange group 166 C) with advancing senescence. The stipules are considered to be early deciduous.

Flowers:

*Flower buds.*—Generally — The floral buds, depending upon the stage of development, are approximately 6.0 millimeters wide; about 10.0 millimeters long; conic in form; and slightly appressed relative to the bearing shoot.

*Flower buds.*—Color — This characteristic is dependent upon the proximity to bloom. The bud scales are deep purple, (approximately RHS Greyed-Purple Group N186 B). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress, and therefore this information is not available.

*Date of first bloom.*—Observed on Mar. 1, 2004.

*Blooming time.*—Considered mid-season in relative comparison to other commercial peach cultivars grown in the central San Joaquin Valley. The date of full bloom was observed on Mar. 6, 2004. The date of full bloom varies slightly with climatic conditions and cultural practices.

*Duration of bloom.*—Approximately 10 days. This characteristic varies slightly with the prevailing climatic conditions.

*Flower type.*—The variety is considered to have a showy type flower.

*Flower size.*—Flower diameter at full bloom is approximately 32.0 to about 36.0 millimeters.

*Bloom quality.*—Considered abundant.

*Flower bud frequency.*—Normally 1 to 2 flower buds appear per node.

*Petal size.*—Generally — Considered medium for the species.

*Length.*—Approximately 15.0 to about 18.0 millimeters.

*Width.*—Approximately 15.0 to about 16.0 millimeters.

*Petal form.*—Considered ovoid.

*Petal count.*—Nearly always 5.

*Petal texture.*—Glabrous.

*Petal color.*—Light pink, (RHS Red-Purple Group 65 B) to a medium pink, (RHS Red-Purple Group 73 C).

*Fragrance.*—Slight.

*Petal claw.*—Form — The claw is considered generally ovoid and has a medium size when compared to other varieties. Length — Approximately 6.0 to about 8.0 millimeters. Width — Approximately 7.0 to about 9.0 millimeters.

*Petal margins.*—Generally considered variable, from nearly smooth to slightly ruffled, to moderately undulate to ruffled.

*Petal apex.*—Generally — The petal apices generally appear entire at the tip.

*Flower pedicel.*—Length — Considered medium-long, and having an average length of approximately 4.0 to about 5.0 millimeters. Diameter — Considered average, approximately 3.0 millimeters. Color — A medium brown, (RHS Brown Group 200 D).

*Floral nectaries.*—Color — A dull orange, (RHS Greyed-Orange Group N172 A).

*Calyx.*—Surface Texture — Generally glabrous. Color — A dull red, (approximately RHS Greyed-Purple Group N186 C).

*Sepals.*—Surface Texture — The surface has a short, fine pubescent texture. Size — Average, and ovate in form. Color — A dull red, (approximately RHS Greyed-Purple Group 183 B).

*Anthers.*—Generally — Average in length. Color — Red to reddish-purple dorsally, (approximately RHS Greyed-Purple Group 187 B).

*Pollen production.*—Pollen is abundant, and has a yellow color, (approximately RHS Yellow-Orange Group 17 B).

*Fertility.*—No pollinator required.

*Filaments.*—Size — Length is variable, approximately 14.0 to about 16.0 millimeters long. Color — Light pink, (RHS Red Group 55 D).

*Pistil.*—Number — Usually 1, rarely 2. Generally — Average in size. Length — Approximately 15.0 to about 17.0 millimeters including the ovary. Color — Pale green, (approximately RHS Yellow-Green Group 145 C). Surface Texture — The variety has a long pubescent pistil.

Fruit:

*Maturity when described.*—Firm ripe condition (shipping ripe).

*Date of first picking.*—Jul. 5th, 2004. Date of last picking. — Jul. 15, 2004. The date of harvest varies slightly with the prevailing climatic conditions.

*Size.*—Generally — Considered large, and uniform.

*Average cheek diameter.*—Approximately 72.0 to about 78.0 millimeters.

*Average axial diameter.*—Approximately 71.0 to about 74.0 millimeters.

*Typical weight.*—Approximately 271.0 grams. This characteristic is highly dependent upon the prevailing cultural practices, and therefore is not particularly distinctive of the variety.

*Fruit form.*—Generally — Considered oblate. The fruit is generally uniform in symmetry.

*Fruit suture.*—Very shallow and appearing almost non-indented. The fruit suture extends from the base to the apex. Slight grooving is typically observed toward the apex. No apparent callousing or stitching exists along the suture line.

*Suture.*—Color — Generally blushed to the same degree as the skin, (approximately RHS Red Group 43 B).

*Ventral surface.*—Form — Only slightly indented.

*Apex.*—Rounded.

*Base.*—Generally retuse.

*Stem cavity.*—Generally rounded and uniform. Average depth of the stem cavity is about 5.0 mm. Average width of the stem cavity is about 15 mm.

*Fruit skin.*—Thickness — Considered medium in thickness, and tenacious to the flesh. Texture — Short, fine and pubescent. The pubescence is moderately abundant. Taste — Non-astringent. Tendency to crack — None observed.

*Color.*—Blush Color — Generally speaking, a red blush exists on a majority of the skin of the fruit (approximately RHS Red Group 42 A), and is typically more present on the basal portions of the fruit. The blush covers approximately 80–90% of the fruit skin surface. The percentage of the blush on the fruit skin surface can vary, and is generally dependent upon the prevailing ecological and cultural conditions under which the fruit was grown. Ground Color — Yellow, (approximately RHS Yellow-Orange Group 19 B).

*Fruit stem.*—Medium in length, approximately 6.0 to about 8.0 millimeters. Diameter — Approximately 2.0 to about 3.0 millimeters. Color — Pale yellow-green, (approximately RHS Yellow-Green Group 144 B).

*Flesh.*—Ripening — Considered even. Texture — Firm, juicy and dense. Considered non-melting. Fibers — Few, small, and tender ones are found. Aroma — Very slight. Eating Quality — Considered very good. Flavor — Considered sweet and mildly acidic. The flavor is considered both pleasant and balanced. Juice Production — Moderate. Brix — About 13.0 degrees. This characteristic varies slightly with the number of fruit per tree; prevailing cultural practices; and the surrounding climatic conditions. Flesh Color — Pale yellow-orange, (approximately RHS Yellow-Orange Group 20C).

Stone:

*Type.*—Clingstone.

*Size.*—Considered medium-large for the variety. The stone size varies significantly depending on tree vigor, crop load and growing conditions.

*Length.*—Average, about 28.0 to about 33.0 millimeters.

*Width.*—Average, about 23.0 to about 27.0 millimeters.

*Diameter.*—Average, about 16.0 to about 19.0 millimeters.

*Form.*—Ovoid.

*Base.*—The stone is usually rounded and considered narrow or slightly elongated relative to the general shape.

*Apex.*—Shape — The stone apex is slightly lobed and generally without a prominent apical tip.

*Stone surface.*—Surface Texture — Typically deep furrowing is observed across the stone surface. Pitting is much less abundant, generally speaking, as compared to the presence of furrowing which is typically noted near the base. Ridges — The most prominent ridges are generally oriented concentrically and perpendicular relative to the stone's longitudinal axis, and are further near the apex of the stone. Toward the base of the stone, the ridges are generally oriented parallel relative to the stone axis. Ventral Edge — Width — Considered medium, and having a dimension of approximately 3.0 to about 4.0 millimeters when measured at the mid-suture. Dorsal Edge — Shape — Full, lightly grooved, and considered reasonably prominent.

*Stone color.*—The color of the dry stone is generally reddish brown, (approximately Greyed-Red Group RHS 178 A). This is variable however, and may be affected by oxidation. In view of this variability, this characteristic cannot be considered distinctive of the variety.

*Tendency to split.*—Splitting has rarely been noted.

*Kernel.*—Size — The kernel is considered medium-large. Form — Considered ovoid. Pellicle — Pubescent. Color — (RHS Greyed-Orange Group N167 B).

*Use.*—The subject variety 'Burpeachtwentyone' is considered to be a peach tree of the late season maturity, and which produces fruit which are considered firm, attractively colored, and which are useful for both local and long distance shipping.

*Keeping quality.*—Excellent. Fruit has stored well up to 25 days after harvest at 1.0 degree Celsius.

*Shipping quality.*—Good. The fruit of the new peach tree variety showed minimal bruising of flesh or skin damage after being subjected to normal harvest and packing procedures.

*Resistance to insects and disease.*—No particular susceptibilities were noted. The present variety has not been tested to expose or detect any susceptibilities or resistances to any known plant and/or fruit diseases.

Although the new variety of peach tree possesses the described characteristics when grown under the ecological conditions prevailing near Fowler, Calif., in the Central part of the San Joaquin Valley of California, it should be understood that variations of the usual magnitude and characteristics incident to changes in growing conditions, fertilization, pruning, pest control and horticultural management are to be expected.

Having thus described and illustrated our new variety peach tree, what we claim is new and desire to secure by Plant Letters Patent is:

1. A new distinct variety of peach tree, substantially as illustrated and described, and which is characterized principally as to novelty by producing an attractively colored yellow-fleshed, clingstone peach which is mature for harvesting approximately July 5 to July 15 under the ecological conditions prevailing in the San Joaquin Valley of central California.

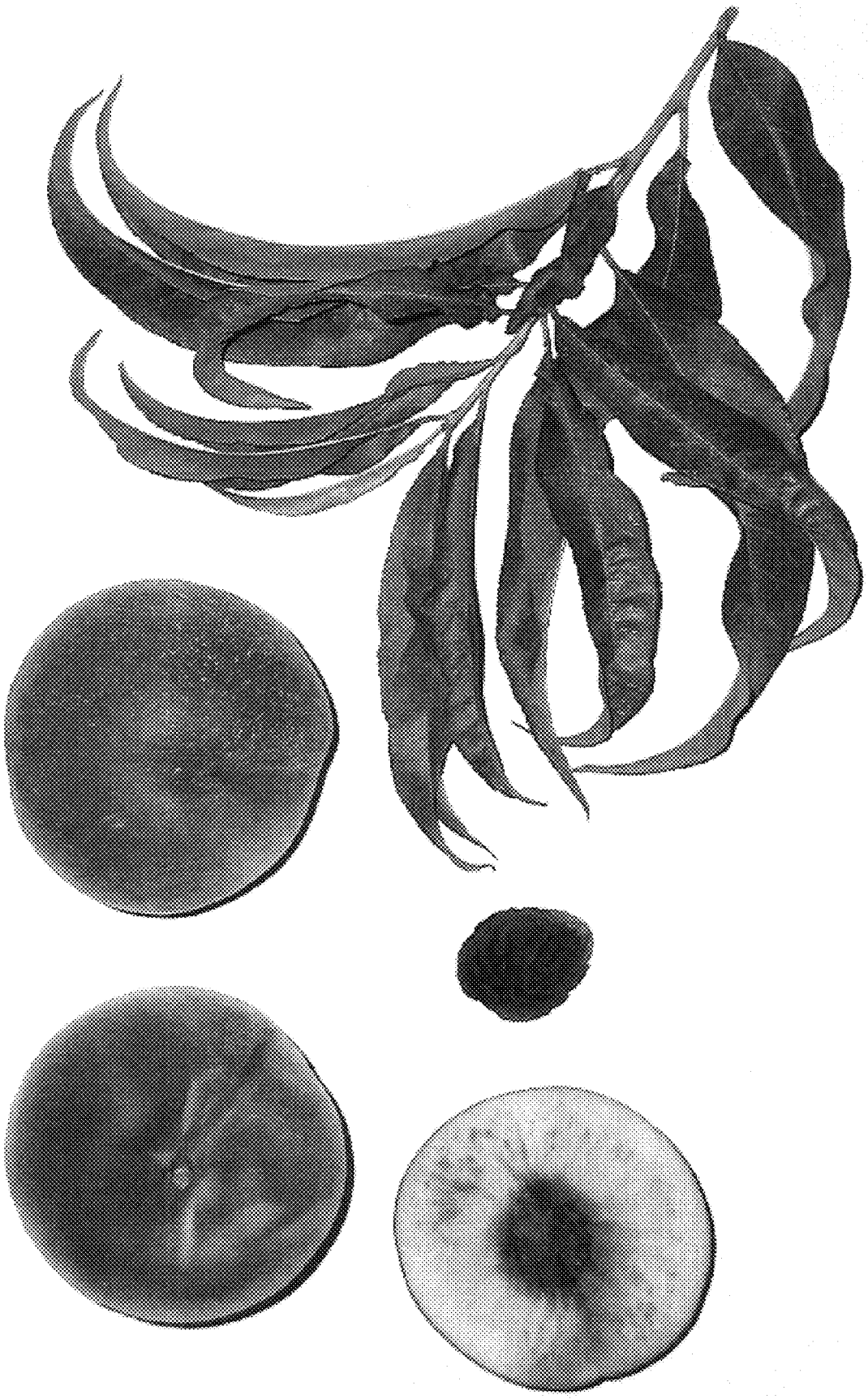

* * * * *